(12) United States Patent
Farren et al.

(10) Patent No.: US 12,266,446 B2
(45) Date of Patent: Apr. 1, 2025

(54) UTILIZING ONE OR MORE MODELS TO AUDIT A PROCESS

(71) Applicant: Mynatek, Inc., Oakland, CA (US)

(72) Inventors: Alexander Raymond Richard Farren, Oakland, CA (US); Richard Samuel Kagan, San Jose, CA (US)

(73) Assignee: Mynatek, Inc., Oakland, CA (US)

(*) Notice: Subject to any disclaimer, the term of this patent is extended or adjusted under 35 U.S.C. 154(b) by 0 days.

(21) Appl. No.: 18/747,154

(22) Filed: Jun. 18, 2024

(65) Prior Publication Data

US 2025/0062015 A1 Feb. 20, 2025

Related U.S. Application Data

(63) Continuation-in-part of application No. 18/671,808, filed on May 22, 2024, which is a continuation of application No. 18/236,824, filed on Aug. 22, 2023, now Pat. No. 12,033,748.

(60) Provisional application No. 63/532,729, filed on Aug. 15, 2023.

(51) Int. Cl.
*G16H 40/20* (2018.01)

(52) U.S. Cl.
CPC .................. *G16H 40/20* (2018.01)

(58) Field of Classification Search
CPC ..................................... G16H 40/20
See application file for complete search history.

(56) References Cited

U.S. PATENT DOCUMENTS

2018/0122506 A1* 5/2018 Grantcharov ........... G06F 17/40
2023/0120290 A1 4/2023 Baarman

FOREIGN PATENT DOCUMENTS

CN 112239120 1/2021
WO WO-2022101860 A1 * 5/2022 ......... B23K 26/0624

OTHER PUBLICATIONS

Cloudd-Based Fault Prediction Using IoT in Office Automation for Improvisation of Health of Employees. Author: Uppal, Mudita, et al. Chitkara University Institute of Engineering and Technology, Chitkara University, Punjab, India. Journal of Healthcare Engineering 2021 Hindawi Limited. (2021) (Year: 2021).*
Bjorlykhaug et al., "Vision System for Quality Assessment of Robotic Cleaning of Fish Processing Plants Using CNN". IEEE Access. vol. 7, 2019 (Year: 2019).
McKinley et al., Evaluation of Daily Environmental Cleaning and Disinfection Practices in Veterans Affairs Acute and Long-Term Care Facilities: A Mixed Methods Study, American Journal of Infection Control, Feb. 2023, vol. 51, Issue 2.
Singh et al., Automatic Detection of Hand Hygiene Using Computer Vision Technology, Journal of the American Medical Informatics Association, 2020, vol. 27 Issue 8.

* cited by examiner

Primary Examiner — Linh Giang Le
(74) Attorney, Agent, or Firm — Van Pelt, Yi & James LLP

(57) ABSTRACT

Data associated with one or more workers performing a task is obtained by one or more sensors. One or more machine learning models trained to determine whether the one or more workers correctly performed the task based on the data associated with the one or more workers performing the task are utilized. A notification indicating whether the one or more workers correctly performed the task is outputted.

22 Claims, 11 Drawing Sheets

900

UTILIZING ONE OR MORE MODELS TO AUDIT A PROCESS

CROSS REFERENCE TO OTHER APPLICATIONS

This application is a continuation in part of U.S. patent application Ser. No. 18/671,808 entitled ARTIFICIAL INTELLIGENCE ENHANCED CLEANING filed May 22, 2024, which is a continuation of U.S. patent application Ser. No. 18/236,824 entitled ARTIFICIAL INTELLIGENCE ENHANCED CLEANING filed Aug. 22, 2023 which claims priority to U.S. Provisional Patent Application No. 63/532,729 entitled ARTIFICIAL INTELLIGENCE ENHANCED CLEANING filed Aug. 15, 2023, each of which is incorporated herein by reference for all purposes.

BACKGROUND OF THE INVENTION

A process is comprised of a plurality of tasks. For the process to be considered to have been completed, each task must be performed to achieve designated acceptance requirements according to specific guidelines and in some designated order, otherwise the process may be considered to have been incomplete and/or not performed so as to meet acceptance requirements. A user may be provided with a checklist, a manual, a guidebook, etc., to assist them with completing the plurality of tasks. However, human error is unavoidable and may be introduced into the process. As a result, one or more errors may be introduced into the process. This may lead to real-world consequences.

For example, hospital staff may be assigned the task of cleaning a room. Certain procedures may be established (e.g., by hospital staff, government regulation, etc.) to ensure that hospital rooms are properly cleaned. Hospitals may audit cleanings to determine whether the hospital staff complied with the established procedures. However, only a small percentage of cleanings are audited because of the costs and lack of staff to perform audits. In the event the hospital staff did not comply with the established procedures and the cleaning was not audited, patients may be exposed to harmful conditions, such as pathogens or toxins on the surfaces that were to be cleaned. If an audit is conducted after the cleaning staff has moved on to the next cleaning a subsequent audit may be unable to fully detect or determine with specificity which of the established procedures the hospital staff failed to comply with. As a result, hospital rooms may need to be recleaned, which causes delays in the admittance of new patients. In a worst case scenario, the room is not recleaned and the room is used for new patients, exposing them to potentially harmful diseases.

BRIEF DESCRIPTION OF THE DRAWINGS

Various embodiments of the invention are disclosed in the following detailed description and the accompanying drawings.

DETAILED DESCRIPTION

Figure 1A:
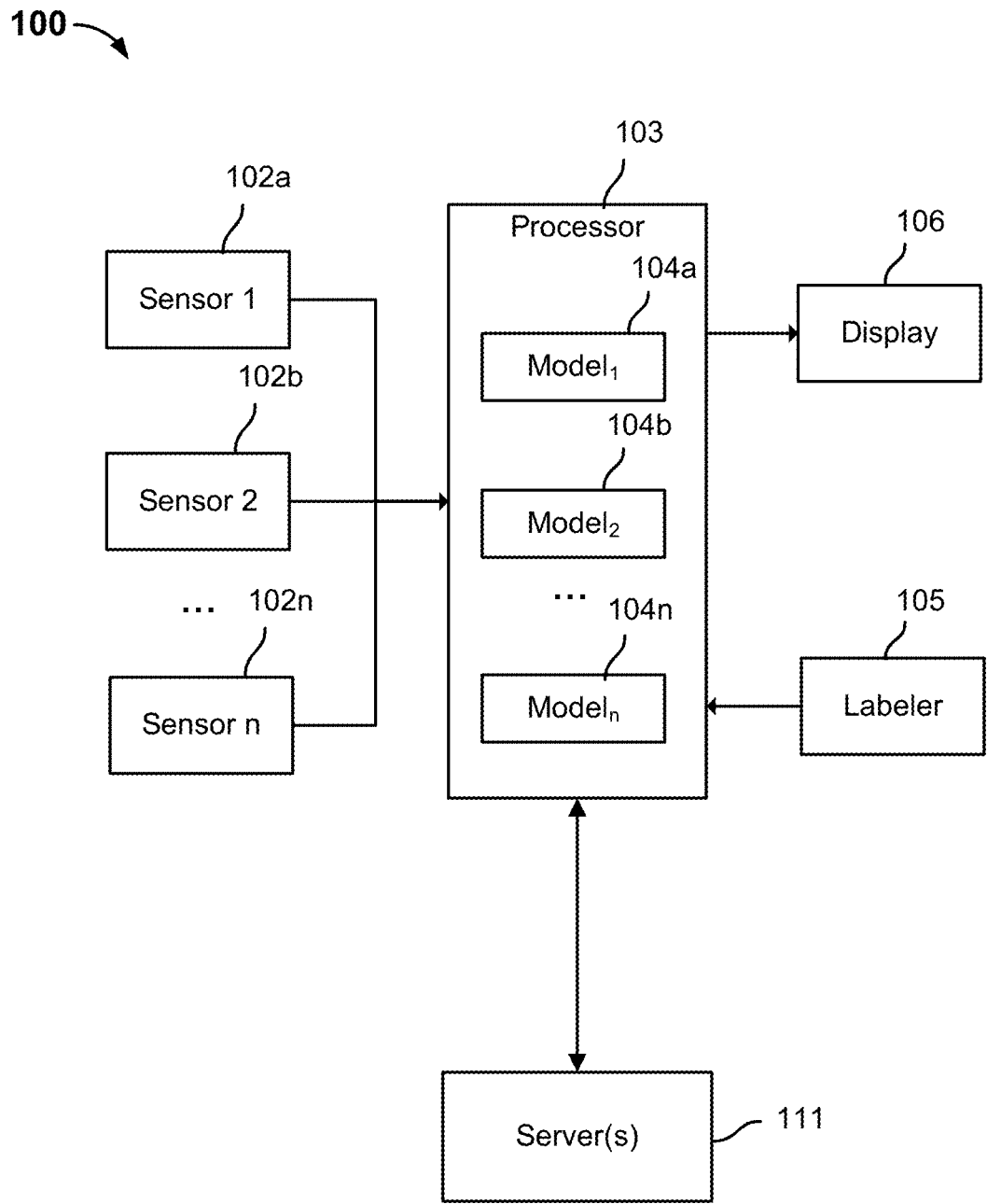
FIG. 1A is a block diagram illustrating a system to audit a process performed by one or more workers in accordance with some embodiments.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

One or more workers may perform a task within a space. Examples of a space include, but are not limited to a room, an elevator, a car, a train, a grocery store, a gym, a studio, a place of worship, a theater, a garage, an airport, a school, a manufacturing plant, a hospital, a healthcare facility, or any other worker occupied space. The one or more workers may haphazardly perform the task or perform the task without any regard to established procedures. For example, the one or more workers may be tasked with cleaning a hospital room, but clean the surfaces of the room without sufficient pressure or sufficient cleaning liquid. Established procedures, such as those outlined by Occupational Safety and Health Administration (OSHA), may dictate how the surfaces of the hospital room are to be cleaned. The inability of the one or more workers to follow the established procedures may lead to undesired real-world consequences, such as patients unintentionally becoming sick in a hospital room after the hospital room is cleaned. Other tasks in the healthcare industry that may be improperly performed, include, but are not limited to, the disinfection of needleless catheter connectors, the insertion of central lines of IV's, the preparation of medications with proper aseptic technique. In other real-world examples, failing to follow established procedures may cause pieces of an airplane to become loose mid-flight after airplane maintenance, a wheel to fall off a vehicle after a tire rotation, etc.

Techniques to audit a process performed by one or more workers (e.g., a human) are disclosed. Although the techniques are described with respect to a hospital room cleaning example, the techniques disclosed herein are applicable to other processes in which proper procedures for each task associated with a process can be established, the correct technique(s) to properly perform the procedures can be articulated, the sensor(s) needed to monitor the procedures being performed can be identified, and the expected sensor output(s) for a correctly performed procedure and an incorrectly performed procedure can be established. Examples of other processes include, but are not limited to: performing a maintenance routine on a vehicle (e.g., car, motorcycle, airplane, helicopter, boat, etc.), surgical operations, drug formulation, construction operations, housekeeping, cooking operations, etc.

The techniques include training one or more machine learning models and/or other types of mathematical models to determine whether a task is being correctly performed. A process may be comprised of one or more tasks. In some embodiments, one or more machine learning models is trained for each of the one or more tasks. In some embodiments, a single machine learning model or other type of mathematical model is trained for the entire process. In some embodiments, a plurality of machine learning models and/or other types of mathematical models are trained for the entire process. A machine learning model may be trained using supervised learning, unsupervised learning, semi-supervised learning, or reinforcement learning. In some embodiments, other types of models are used, such as heuristic models, statistical models, etc. A combination of machine learning and other types of models may be implemented to determine whether a task is being correctly performed.

For embodiments that utilize machine learning, one or more trainers (e.g., humans) are used to train the one or more machine learning models. The one or more trainers perform the task according to the established procedures, and also perform the tasks in ways that do not conform to the established procedures. Data associated with the one or more trainers performing the task is received from a plurality of sensors and provided to a processing system. Each data set produced by the sensors is labeled by the trainers or by others with knowledge of how each task should be performed, indicating whether the sensor data is associated with a correct or incorrect performance of the task. In some embodiments, the training data sets may be labeled by a processing system that has been trained on correct and incorrect performance of the task. The sensor(s) used to train the one or more machine learning models or other models depend on the task being performed.

A process is comprised of one or more tasks. In some embodiments, for a process that includes a plurality of tasks, a first set of sensors is used for a first task and a second set of sensors is used for a second task where at least one sensor from the first set of sensors is not included in the second set of sensors. For each task, a processing system may determine which sensor(s) are relevant to the task, filter out data associated with non-relevant sensor(s), and generate a feature vector utilizing the data associated with the relevant sensor(s). The feature vector includes one or more quantitative or qualitative values. The one or more quantitative or qualitative values may be a sensor value, a value derived from a sensor value, or a value based on an observation associated with the sensor value(s) (e.g., a label). In some embodiments, a same set of sensors is used for the one or more tasks. For each task, a processing system may generate a feature vector utilizing the data associated with the sensors. For example, in some embodiments, a process to analyze the installation of components of a plane could be implemented to aid with manual inspection protocols. Based on initial data received from the plane manufacturing or maintenance company, the system analyzes the images and specifications to determine the most suitable sensors needed for effective monitoring. It concludes that a combination of optical cameras, thermal cameras, strain gauges, and ultrasonic sensors will be optimal for this environment. The optical cameras will monitor the performance of an installation task, the thermal cameras will tasks that cause materials to change temperature properties, the strain gauges will measure physical stress on components as they're handled, installed or removed, and the ultrasonic sensors will identify if tasks induce cracks or delaminations.

In some embodiments, the processing system is configured to process the sensor data into a usable format. For example, the processing system may preprocess the image data and extract one or more features or patterns utilizing computer vision. Computer vision may be utilized to recognize gestures and/or actions performed by the one or more workers. The one or more features or patterns may include edges, shapes, textures, colors, gestures, actions, etc. The extracted features/patterns and their corresponding values may be used as part of the feature vector.

A sensor value is included as part of a feature vector to a machine learning model or other type of mathematical model. In some embodiments, sensor values over a period of time are provided as a series of feature vectors to a machine learning model or other type of mathematical model. In some embodiments, one or more transformations are applied to a sensor value and the transformed value is included as part of a feature vector to a machine learning model or other type of mathematical model.

The one or more trainers perform the task according to the established procedures to generate a set of training data. Each time the one or more trainers perform the task, a labeler (human or model) may review the results of task and label a result of the performance as being correct, partially correct, or incorrect. In some embodiments, the one or more labelers score the performance with a numerical value, such as a score on a scale from 1-10, 1-100%, a qualitative value, such as "very bad," "bad," "okay," "good," and "very good," or some other metric. In some embodiments, the label is included as part of the feature vector inputted to the one or more machine learning models being trained. The one or more trainers repeatedly perform a task until the one or more machine learning models are capable of outputting a prediction having a confidence value above a threshold value. The one or more machine learning models may be trained using videos of a task being correctly performed in conjunction with one or more other sensor values indicating the task is being correctly performed. The prediction indicates whether or not the one or more trainers correctly perform the task. This process may be repeated for the one or more tasks associated with a process.

The one or more sensors are implemented in a production environment under real-world conditions and the one or more trained machine learning models and/or other mathematical models obtain data from the one or more sensors. For example, the one or more sensors may be implemented in a hospital, a vehicle garage, an airport hangar, etc. The one or more trained machine learning models output a prediction having a confidence value associated with a task. The prediction indicates whether one or more workers correctly performed the task. For a process comprised of a plurality of tasks, at least one of the one or more trained machine learning models outputs a corresponding prediction associated with a task of the plurality of tasks.

A notification is provided based on an output of the one or more trained machine learning models and/or mathematical models. In some embodiments, the notification is provided at the completion of a task. At the completion of the task, the post-task notification may be provided to a device associated with the one or more workers to provide real-time feedback. The post-task notification may include an indication (e.g., pass/fail) indicating whether the one or more workers correctly performed the task. The post-task notification may include comments indicating why the one or more workers incorrectly performed the task. The comments may be learned from feedback provided by a labeler when training the one or more trained machine learning models. The post-task notification may include one or more recommendations indicating what the one or more workers may do to correctly perform the task. For example, a user interface (graphical or text) may indicate one or more surfaces in a space that one or more cleaners failed to clean properly. The post-task notification may include information indicating how to correctly perform the task. For an indicated task, the post-task notification may include step(s) that need to be taken to correct the problems. In response to receiving the post-task notification, the one or more workers may repeat the task.

In some embodiments, the notification is provided at the completion of a process. At the completion of the process, the notification may be provided to a device associated with the one or more workers to provide real-time feedback. The notification may also be provided to one or more servers (e.g., on-prem or cloud servers) so that a report associated with a completion of the process may be generated. This enables a person managing the one or more workers to review their work. The post-process notification may include the same information as a post-task completion notification. In addition, in some embodiments, the post-process notification indicates that all of the one or more tasks associated with the process were correctly completed. In some embodiments, the post-process notification indicates at least one of the one or more tasks associated with the process was incorrectly completed. The post-process notification may indicate which of the one or more tasks associated with the process was incorrectly completed. For an indicated task, the post-process notification may include comments indicating why the one or more workers incorrectly performed the task. For an indicated task, the post-process notification may include step(s) that need to be taken to correct the problems.

The process may be periodically (e.g., daily, weekly, bi-monthly, monthly, biannually, annually, etc.) audited to determine whether the process is correctly being performed. One or more reviewers may review the process performed by the one or more workers and an output of the one or more trained machine learning models (and other mathematical models). For example, the one or more reviewers may swab a hospital room to detect levels of a particular pathogen after the room was cleaned by one or more workers or the one or more reviewers may check different parts of a vehicle to ensure that they were properly tightened after a maintenance procedure was performed. The reviewer's results are compared to an output of the one or more trained machine learning models (or other mathematical models). In response to a determination that the reviewer's results agree with the output of the one or more trained machine learning models (or other mathematical models), the one or more trained machine learning models (or other mathematical models) may continue to be implemented in the production environment. In response to a determination that the reviewer's results do not agree with the output of at least one of the one or more trained machine learning models (or other mathematical models), a setup associated with the production environment is recalibrated. In some embodiments, the one or more trained machine learning models (or other mathematical models) are retrained. In some embodiments, some or all of the sensors associated with a task are modified or replaced. For example, a sensor may be out of position and no longer providing accurate measurements. A sensor may fail and need to be replaced. A sensor may provide inaccurate measurements because it needs new batteries. A component used in the process may have changed and the tasks associated may have also changed. Recalibrating the setup associated with the production environment ensures the one or more workers are accurately audited.

FIG. 1A is a block diagram illustrating a system to audit a process performed by one or more workers in accordance with some embodiments. In the example shown, system 100 includes sensors 102a, 102b, . . . , 102n. Although FIG. 1A illustrates system 100 having three sensors, system 100 may include 1: n sensors. Sensors 102a, 102b, . . . , 102n may be installed at various locations throughout a space.

In some embodiments, one or more items may be affixed to an object to enhance the collection of sensor data associated with the object. For example, metallic objects, such as IV poles, do not emit significant IR light and they may reflect IR light (e.g., light coming in through a window). This may make it difficult to obtain useful thermal data from the metallic object. However, if an emissive/non-reflective label (e.g., a piece of black tape) is affixed to the metallic object, it becomes possible to determine from the thermal change on the label that the metallic object has been wiped.

In some embodiments, one or more items may be used in conjunction with a sensor to enhance the collection of sensor data associated with an object. For example, adding a special light source, such as an IR illuminator, or a laser may enable a single thermal sensor to work without an image sensor. An additional exciter (e.g., optical, IR, acoustic, etc.) may be used with a sensor or one or more objects may be affixed to an object to reduce detecting false positives based on the sensor data.

In some embodiments, sensors 102a, 102b, . . . , 102n include at least two different types of sensors. For some tasks, this prevents over reliance on the data associated with a particular sensor when determining whether a task was correctly performed. For example, a first sensor may be an image sensor and a second sensor may be a thermal sensor.

When a worker is cleaning a surface, the image sensor data may indicate the worker moved a cleaning towel on the surface, however, the thermal sensor data may indicate that portions of the surface were not contacted by the cleaning towel or that the cleaning towel did not apply a sufficient amount of cleaning liquid to the surface. Solely relying on the image sensor data may lead to an incorrect determination that the surface was properly cleaned. Adding the additional sensor type may prevent false positives or false negatives from occurring. Sensors 102a, 102b, . . . , 102n may be an image sensor, a thermal sensor, a pressure sensor, a torque sensor, a temperature sensor, a radiation sensor, a proximity sensor, a position sensor, a flow sensor, a contact sensor, an acoustic sensor, a light sensor, a radar sensor, a millimeter wave sensor, an ultrasonic sensor, a touch sensor, an accelerometer, a humidity sensor, an infrared sensor, a light sensor, a color sensor, a gas sensor, a gyroscope, a hall sensor, a capacitive sensor, an analog sensor, a photoelectric sensor, a level sensor, a chemical sensor, an optical sensor, an active sensor, a force sensor, etc. The sensors 102a, 102b, . . . , 102n are selected based on the task being performed. The locations of the sensors 102a, 102b, . . . , 102n are selected based on the task being performed. For example, a pressure sensor may be located in a glove that a mechanic is wearing to determine whether the mechanic is providing a sufficient amount of force to a tool when performing a maintenance task.

In some embodiments, at least two of the sensors 102a, 102b, . . . , 102n are the same type of sensors and one of the sensors 102a, 102b, . . . , 102n is a different type of sensor. For example, at least two of the sensors 102a, 102b, . . . , 102n may be image sensors and one of the sensors 102a, 102b, . . . , 102n is a thermal sensor.

A process is comprised of one or more tasks. For a single task process, a single set of sensors is used. In some embodiments, for a multi-task process, a single set of sensors is used. In some embodiments, for a multi-task process, multiple sets of sensors are used. The multiple sets of sensors include at least one sensor that is not included in all of the sets of sensors.

Sensors 102a, 102b, . . . , 102n are connected (wired or wirelessly) to processor 103. Processor 103 may be included in a server, a computer, a laptop, a desktop, a tablet, a smartphone, etc. In some embodiments, a sensor is configured to continuously provide data to processor 103. In some embodiments, a sensor is configured to periodically provide data to processor 103. In some embodiments, a sensor is configured to provide data to processor 103 in response to a change in state. The sensor data may be analog data or digital data. In some embodiments, processor 103 is located in the same space as the sensors 102a, 102b, . . . , 102n. In some embodiments, processor 103 is located in the same building but a different space than sensors 102a, 102b, . . . , 102n. In some embodiments, processor 103 is located on the same network as sensors 102a, 102b, . . . , 102n (e.g., different buildings, same network).

In some embodiments, processor 103 is configured to process the sensor data into a usable format. For example, processing 103 may preprocess image data and extract one or more features or patterns utilizing computer vision. Computer vision may be utilized to recognize gestures and/or actions performed by the one or more workers. The one or more features or patterns may include edges, shapes, textures, colors, gestures, actions, etc. The extracted features/patterns and their corresponding values may be used as part of a feature vector.

Processor 103 includes models 104a, 104b, . . . , 104n. Although FIG. 1A illustrates processor 103 having three models, processor 103 may include 1: n models. For a single task process, processor 103 may include one or more models. In some embodiments, for a multi-task process, processor 103 includes one or more corresponding models for each task. A model may be a machine learning model trained using supervised learning, unsupervised learning, semi-supervised learning, and/or reinforcement learning. A model may be a heuristic model, a statistical model, or other type of mathematical model. The models 104a, 104b, . . . , 104n may be a combination of machine learning model(s), heuristic model(s), statistical model(s), or other type of mathematical model(s).

One or more trainers are used to train the one or more machine learning models associated with a task. The one or more trainers perform the task according to the procedures associated with the task. Data associated with the one or more trainers performing the task is obtained by some or all of sensors 102a, 102b, . . . , 102n. The obtained data is provided to processor 103 to generate a feature vector. The feature vector may be comprised of one or more sensor values, values derived from sensor values, labels, or other information. In some embodiments, the feature vector includes data associated with all of the sensors 102a, 102b, . . . , 102n. In some embodiments, processor 103 receives data from all of the sensors 102a, 102b, . . . , 102n, but data from a subset of sensors 102a, 102b, . . . , 102n is used to determine whether a task was correctly performed. Processor 103 may determine which sensors of the sensors 102a, 102b, . . . , 102n are relevant to the task, filter out data associated with non-relevant sensors (e.g., the non-relevant sensors are relevant to a different task of the process), and generate a feature vector utilizing the data associated with the relevant sensors.

In some embodiments, the feature vector is utilized to train one or more of the machine learning models. In some embodiments, a plurality of feature vectors (e.g., a feature matrix) is utilized to train one or more of the machine learning models. For example, the sensor values over a particular period of time are used to determine whether one or more workers correctly performed a task. In some embodiments, one or more transformations are applied to a sensor value and the transformed value is included as part of a feature vector to a machine learning model.

The one or more trainers perform the task according to the task procedures to generate a training set of data. Labeler 105 (in person, via a live-feed, via a video recording) observes the one or more trainers performing the task. After the one or more trainers have completed their task, labeler 105 may provide an input to processor 103 indicating whether one or more trainers correctly performed the task. The input may be a label (e.g., pass/fail). The label may score the performance with a numerical value, such as a score on a scale from 1-10, 1-100%, a qualitative value, such as "very bad," "bad," "okay," "good," and "very good," or some other metric. The input may be a description of task performance. Processor 103 may perform natural language processing on the description to generate a label for the performance. In some embodiments, the label is included as part of the feature vector. The one or more trainers repeatedly perform a task until the one or more machine learning models associated with the task are capable of outputting a prediction having confidence value above a threshold value. The prediction indicates whether or not the one or more trainers correctly performed the task. This process may be repeated for the one or more tasks associated with a process.

After the models 104a, 104b, . . . , 104n are trained, they are configured to obtain data from one or more sensors implemented in a production environment (e.g., operating under real-world conditions). The models 104a, 104b, . . . , 104n may be hosted on one or more on-prem servers, one or more remote servers, and/or a combination of one or more on-prem servers and one or more remote servers. After the models 104a, 104b, . . . , 104n are trained, they can be applied to identify and locate specific objects or regions of interest within images or videos. Object detection algorithms can identify and outline multiple objects simultaneously, while object recognition algorithms can classify the detected objects into specific categories. Artificial intelligence provides the intelligence to make accurate predictions and improve the overall accuracy of object detection and recognition systems.

Processor 103 is connected (wirelessly or wired) to display 106. Display 106 may be a monitor, a tablet, a smart device, or any other electronic device having a graphical or text user interface. Display 106 may be owned by a business associated with system 100 or a device owned by the one or more workers. One or more workers may perform a task associated with a process. Processor 103 is configured to provide based on an output of the one or more models a notification to display 106 to provide real-time feedback. In some embodiments, the notification is provided at the completion of a task. The post-task notification may include an indication (e.g., pass/fail) indicating whether the one or more workers correctly performed the task. The post-task notification may include comments indicating why the one or more workers incorrectly performed the task. The post-task notification may include one or more recommendations indicating what the one or more workers may do to correctly perform the task. For example, a user interface (graphical or text) may indicate one or more surfaces in a space that one or more cleaners failed to clean properly. The post-task notification may include information indicating how to correctly perform the task. For an indicated task, the post-task notification may include step(s) that need to be taken to correct the problems. In response to receiving the post-task notification, the one or more workers may repeat the task and remedy the error(s) identified by the notification. There are consequences in not remedying the error(s) (e.g., occupants in a hospital room can become sick). Presenting the error(s) and allowing the one or more workers to remedy the errors may prevent or reduce the likelihood of the consequences from occurring.

In some embodiments, the notification is provided at the completion of a process. At the completion of the process, the notification may be provided to device 106 to provide real-time feedback. The notification may also be provided to one or more servers 111 so that a report associated with a completion of the process may be generated. This enables a person managing the one or more workers to review their work. The post-process notification may include the same information as a post-task completion notification. In addition, in some embodiments, the post-process notification indicates that all of the one or more tasks associated with the process were correctly completed. In some embodiments, the post-process notification indicates at least one of the one or more tasks associated with the process was incorrectly completed. The post-process notification may indicate which of the one or more tasks associated with the process was incorrectly completed. For an indicated task, the post-process notification may include comments indicating why the one or more workers incorrectly performed the task. For an indicated task, the post-process notification may include step(s) that need to be taken to correct the problems.

In some embodiments, processor 103 generates an audit report for the process after the one or more tasks associated with the process has been completed.

In some embodiments, the one or more servers 111 are located on-prem. In some embodiments, the one or more servers 111 are located in a remote facility (e.g., datacenter). In some embodiments, the one or more servers 111 are located in a cloud environment. The cloud environment may be a public cloud, a private cloud, or a hybrid cloud. In some embodiments, processor 103 is located in a cloud environment. In some embodiments, processor 103 is configured to provide to the one or more servers 111 the sensor data received from one or more of the sensors 102a, 102b, . . . , 102n. In some embodiments, processor 103 is configured to provide to the one or more servers 111 one or more notifications associated with a process being performed. In response to receiving the sensor data and/or the notifications the one or more servers 111 may generate an audit report.

Figure 1B:
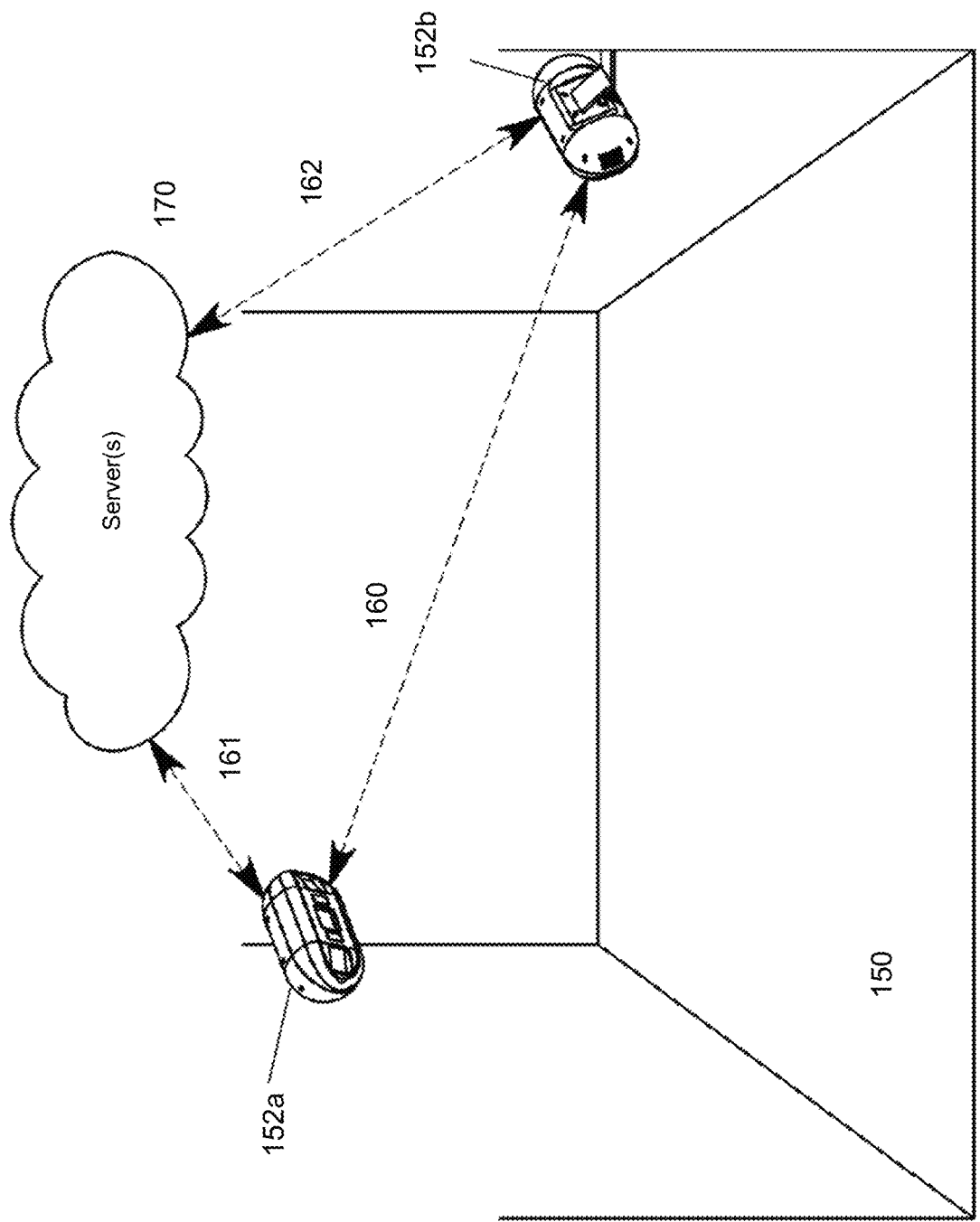
FIG. 1B is a block diagram illustrating a system to audit a process performed by one or more workers in accordance with some embodiments.

FIG. 1B is a block diagram illustrating a system to audit a process performed by one or more workers in accordance with some embodiments. In the example shown, space 150 includes a device 152a having one or more sensors and a second device 152b having one or more sensors. Although FIG. 1B illustrates space 150 have two devices, space 150 may include 1: n devices.

Device 152a and device 152b may communicate with each other via communication link 160 (e.g., Wi-Fi, Bluetooth, Ethernet, etc.). Device 152a and device 152b may include a processor, such as processor 103. In some embodiments, device 152a and device 152b independently determine whether one or more workers in space 150 are correctly performing a task. In some embodiments, device 152a and device 152b jointly determine whether one or more workers in space 150 are correctly performing a task. Data from sensors included in device 152a may be shared with the processor in device 152b. Data from sensors included in device 152b may be shared with the processor in device 152a. In some embodiments, the data from the sensors included in device 152a and device 152b are shared with a processor located outside of space 150. Devices 152a, 152b may communicate with one or more servers located in cloud environment 170 via communication links 161, 162, respectively.

Figure 2:
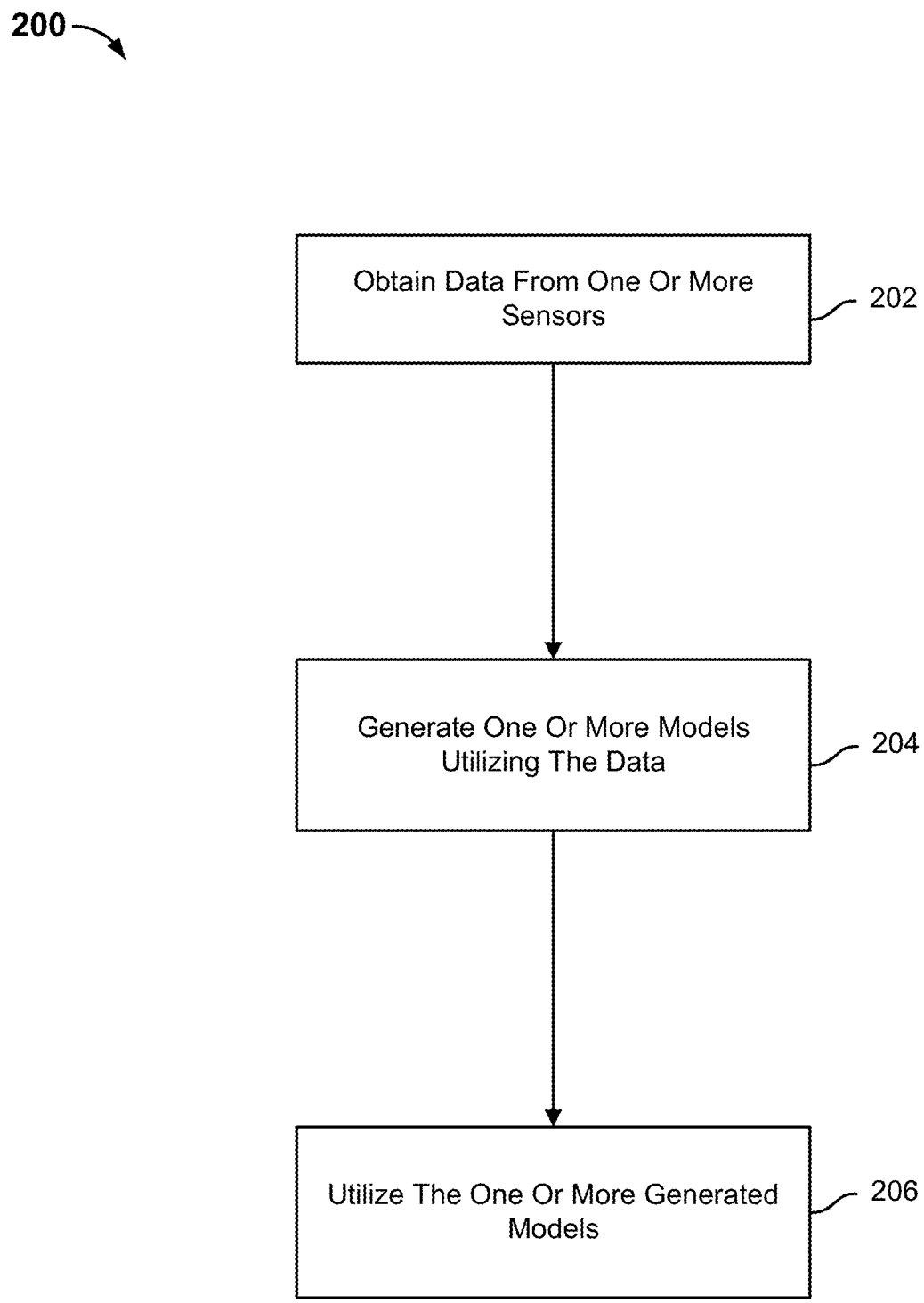
FIG. 2 is a flow diagram illustrating a process to train one or more models in accordance with some embodiments.

FIG. 2 is a flow diagram illustrating a process to train one or more models in accordance with some embodiments. In some embodiments, process 200 is implemented by a processor, such as processor 103. In some embodiments, process 200 is implemented by a server, such as cloud server 111.

At 202, data is obtained from one or more sensors. The sensors may include an image sensor, a thermal sensor, a pressure sensor, a torque sensor, a temperature sensor, a radiation sensor, a proximity sensor, a position sensor, a flow sensor, a contact sensor, an acoustic sensor, a light sensor, a radar sensor, a millimeter wave sensor, an ultrasonic sensor, a touch sensor, an accelerometer, a humidity sensor, an infrared sensor, a light sensor, a color sensor, a gas sensor, a gyroscope, a hall sensor, a capacitive sensor, an analog sensor, a photoelectric sensor, a level sensor, a chemical sensor, an optical sensor, an active sensor, a force sensor, etc.

A sensor is positioned at a location particular to the task being audited. In some embodiments, a single sensor is located within a space at a location that enables optimal sensor measurements associated with a task to be obtained. In some embodiments, a plurality of sensors is positioned at various locations within a space. In some embodiments, a single device includes two or more sensors and the two or more sensors are co-located together at a location associated with the single device. In some embodiments, a first device includes a first set of one or more sensors at a first location within the space and one or more other devices include one or more other sets of one or more sensors at one or more other locations within the space.

At 204, one or more models are generated utilizing the data. In some embodiments, one or more machine learning models are trained utilizing the data. A process is comprised of one or more tasks. One or more workers perform one or more tasks within the space. Utilizing the data obtained from the plurality of sensors, for each task, the one or more machine learning models are trained to output a prediction having a confidence value above a threshold value indicating whether the one or more workers correctly performed the task. Other models, such as a heuristic model, a statistical model, or other types of mathematical model may be generated for the task. In some embodiments, a combination of machine learning model(s), heuristic model(s), statistical model(s), and/or other type of mathematical model(s) are generated for the task.

In some embodiments, the sensor data is processed in a usable format. For example, image data is preprocessed and one or more features or patterns are extracted from the preprocessed image data utilizing computer vision. Computer vision may be utilized to recognize gestures and/or actions performed by the one or more workers. The one or more features or patterns may include edges, shapes, textures, colors, gestures, actions, etc. The extracted features/patterns and their corresponding values may be included as part of one or more feature vectors used to train the one or more machine learning models.

The one or more machine learning models may be trained using supervised learning, unsupervised learning, semi-supervised learning, and/or reinforcement learning. For supervised learning, a labeler may label a performance of the one or more workers performing a task. The label is included as part of a feature vector that includes some or all of the sensor data. In some embodiments, the labeler observes the one or more workers (e.g., in person, via a video feed, a video recording) and labels the performance based on the sensor data or some other measurable metric. In some embodiments, the labeler observes the one or more workers after the task has been performed and labels the performance based on the sensor data (e.g., a video feed coupled with thermal data).

The feature vector is inputted into the one or more machine learning models. The one or more trainers repeatedly perform a task and the one or more machine learning models are adjusted until they output a prediction having a confidence level above a threshold indicating the one or more trainers correctly performed the task. Step 204 may be performed for each task associated with a process.

At 206, the one or more generated models are utilized to determine whether the one or more workers correctly performed the task based on the data obtained from one or more sensors implemented in a production environment. A notification associated with a task is provided based on an output of the one or more models. In some embodiments, the notification is provided after the task is completed. At the completion of the task, the post-task notification may be provided to a device associated with the one or more workers to provide real-time feedback. The post-task notification may include an indication (e.g., pass/fail) indicating whether the one or more workers correctly performed the task. The post-task notification may include comments indicating why the one or more workers incorrectly performed the task. The post-task notification may include one or more recommendations indicating what the one or more workers may do to correctly perform the task. For example, a user interface (e.g., graphical or text) may indicate one or more surfaces in a space that one or more cleaners failed to clean properly. The post-task notification may include information indicating how to correctly perform the task. In response to receiving the post-task notification, the one or more workers may repeat the task. For an indicated task, the post-task notification may include step(s) that need to be taken to correct the problems.

In some embodiments, the notification is provided at the completion of a process. At the completion of the process, the notification may be provided to a device associated with the one or more workers to provide real-time feedback. The notification may also be provided to one or more servers (e.g., cloud or local servers) so that a report associated with a completion of the process may be generated. This enables a person managing the one or more workers to review their work. The post-process notification may include the same information as a post-task completion notification. In addition, in some embodiments, the post-process notification indicates that all of the one or more tasks associated with the process were correctly completed. In some embodiments, the post-process notification indicates at least one of the one or more tasks associated with the process was incorrectly completed. The post-process notification may indicate which of the one or more tasks associated with the process was incorrectly completed. For an indicated task, the post-process notification may include comments indicating why the one or more workers incorrectly performed the task. For an indicated task, the post-process notification may include step(s) that need to be taken to correct the problems.

Figure 3A:
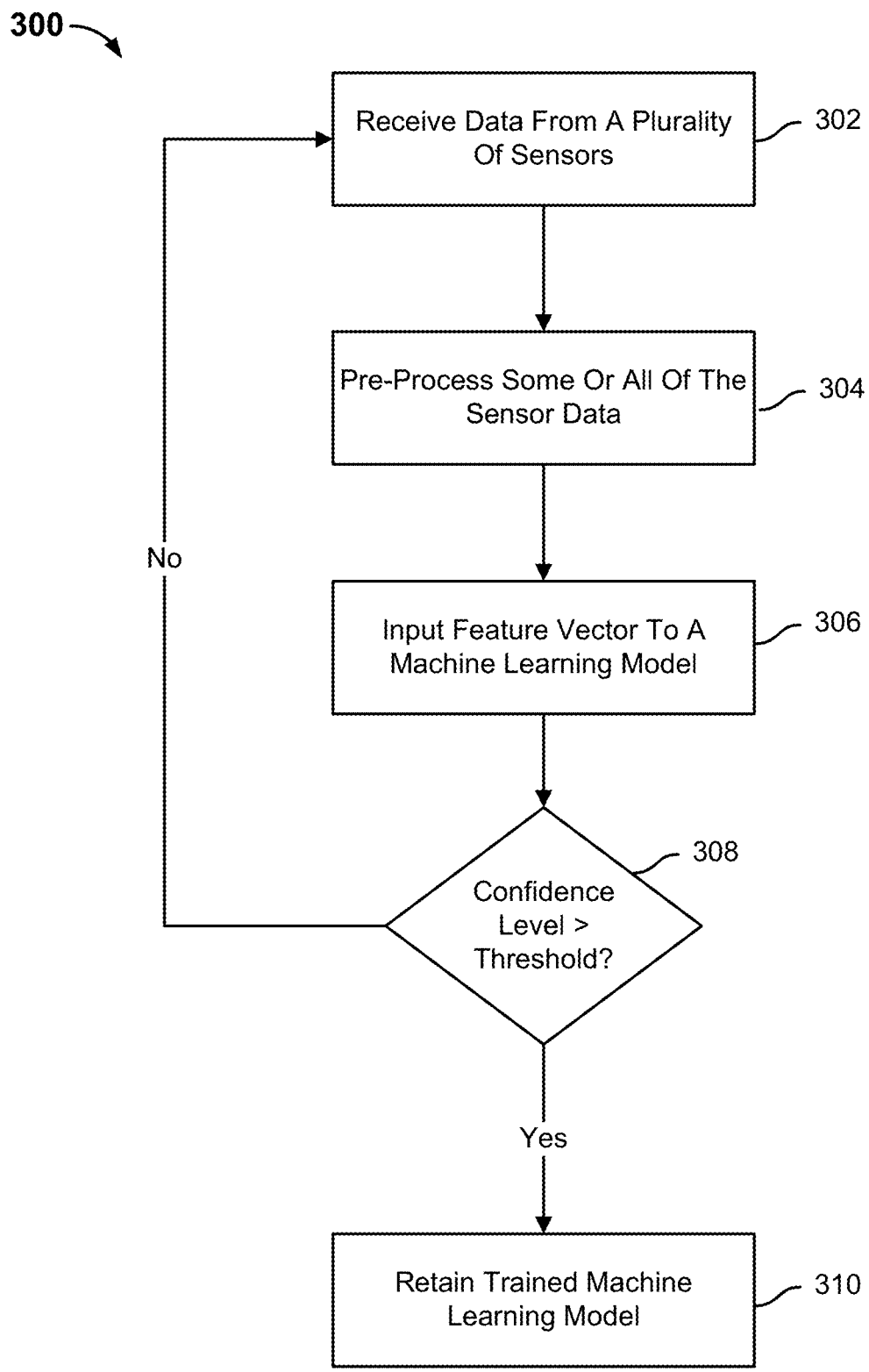
FIG. 3A is a flow diagram illustrating a process to train a machine learning model in accordance with some embodiments.

FIG. 3A is a flow diagram illustrating a process to train a machine learning model in accordance with in accordance with some embodiments. In the example shown, process 300 may be implemented by a processor, such as processor 103. In some embodiments, process 300 is implemented to perform some or all of step 204 of process 200. In some embodiments, process 300 is implemented for a task associated with a process. Process 300 may be repeated for a process with multiple tasks.

At 302, data is received from a plurality of sensors. The data is received from the plurality of sensors while one or more trainers are performing a task.

At 304, some or all of the sensor data is pre-processed. Some of the sensor data may be received from an image sensor, such as a camera. The image data may be preprocessed to enhance image quality, remove noise, correct distortions, or adjust lighting conditions. Preprocessing techniques may involve resizing, filtering, or transforming the data.

The pre-processed image data may be analyzed to extract relevant features or patterns. These features may include edges, shapes, textures, colors, or other complex visual characteristics. Computer vision may be utilized to recognize gestures and/or actions performed by the one or more trainers.

At 306, a feature vector is inputted to a machine learning model to be trained. In some embodiments, the feature vector is used to train a plurality of machine learning models associated with a task.

The feature vector includes some or all of the data received from the plurality of sensors. In some embodiments, the feature vector includes the features extracted from some of the pre-processed sensor data. A labeler reviews a task performed by one or more trainers. The labeler may label a performance of the task. The label may be included as part of the feature vector. In some embodiments, data received from the plurality of sensors is aggregated over a particular period of time and a plurality of feature vectors (e.g., feature matrix) is inputted to the machine learning model to be trained.

An AI algorithm, such as a deep learning model, is trained on labeled datasets to learn patterns and relationships between the extracted features and the corresponding labels or annotations. The training process involves presenting the AI algorithm with a number of labeled examples to optimize the model's parameters to learn the relationships between the input features and the corresponding labels or annotations, allowing it to generalize and make predictions or classifications on new, unseen data. This training enables the model to recognize patterns, objects, or scenes within visual data.

At 308, it is determined whether the machine learning model outputs a prediction having a confidence level above a threshold. The prediction indicates whether the one or more trainers correctly performed a task. In response to a determination that the machine learning model outputs a prediction having a confidence level above the threshold, process 300 proceeds to step 310. In response to a determination that the machine learning model outputs a prediction confidence level that is not above the threshold, process 300 returns to step 302.

At 310, the trained machine learning model is retained in a memory or storage associated with a processor.

Figure 3B:
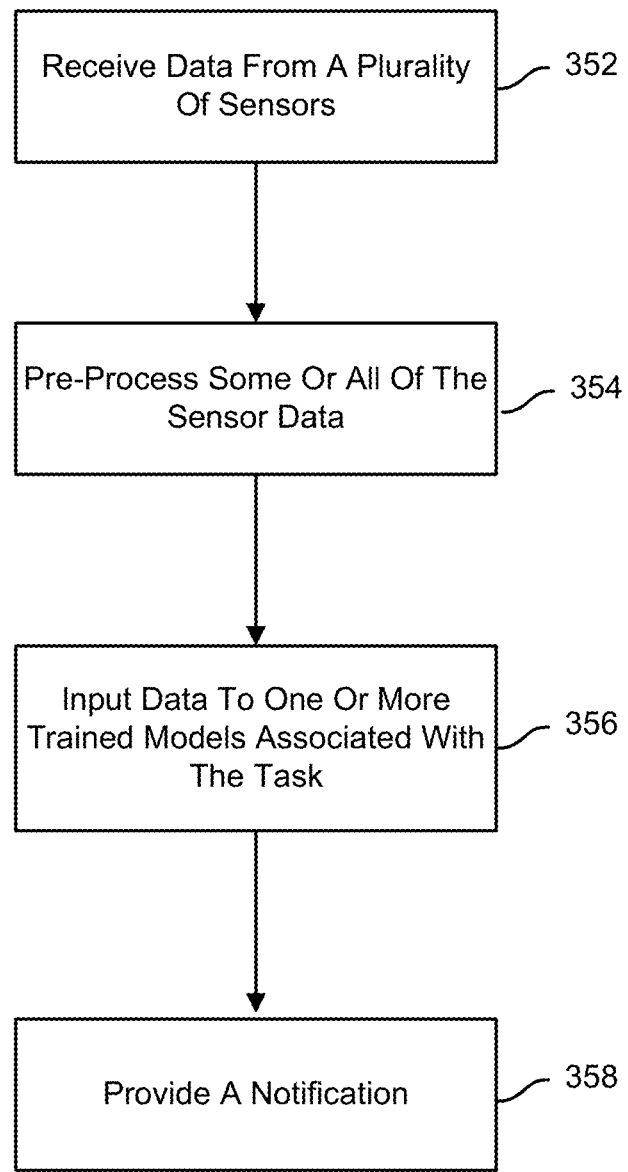
FIG. 3B is a flow diagram illustrating a process to implement a trained model in accordance with some embodiments.

FIG. 3B is a flow diagram illustrating a process to implement a trained model in accordance with some embodiments. In the example shown, process 350 may be implemented by a processor, such as processor 103. In some embodiments, process 350 is implemented to perform some or all of step 206 of process 200. In some embodiments, process 350 is implemented for a task associated with a process. Process 350 may be repeated for a process with multiple tasks.

At 352, data is received from a plurality of sensors. The data is received from the plurality of sensors while one or more workers are performing a task.

At 354, some or all of the sensor data is pre-processed.

At 356, the data is inputted to one or more trained models associated with a task.

At 358, a notification is provided based on an output of the one or more trained machine learning models and/or other models. In some embodiments, the notification is provided at the completion of a task. At the completion of the task, the post-task notification may be provided to a device associated with the one or more workers to provide real-time feedback. The post-task notification may include an indication (e.g., pass/fail) indicating whether the one or more workers correctly performed the task. The post-task notification may include comments indicating why the one or more workers incorrectly performed the task. The post-task notification may include one or more recommendations indicating what the one or more workers may do to correctly perform the task. For example, a user interface (graphical or textual) may indicate one or more surfaces in a space that one or more cleaners failed to clean properly. The post-task notification may include information indicating how to correctly perform the task. For an indicated task, the post-task notification may include step(s) that need to be taken to correct the problems. In response to receiving the post-task notification, the one or more workers may repeat the task.

In some embodiments, the notification is provided at the completion of a process. At the completion of the process, the notification may be provided to a device associated with the one or more workers to provide real-time feedback. The notification may also be provided to one or more servers (e.g., on-prem or cloud servers) so that a report associated with a completion of the process may be generated. This enables a person managing the one or more workers to review their work. The post-process notification may include the same information as a post-task completion notification. In addition, in some embodiments, the post-process notification indicates that all of the one or more tasks associated with the process were correctly completed. In some embodiments, the post-process notification indicates at least one of the one or more tasks associated with the process was incorrectly completed. The post-process notification may indicate which of the one or more tasks associated with the process was incorrectly completed. For an indicated task, the post-process notification may include comments indicating why the one or more workers incorrectly performed the task. For an indicated task, the post-process notification may include step(s) that need to be taken to correct the problems.

Figure 4:
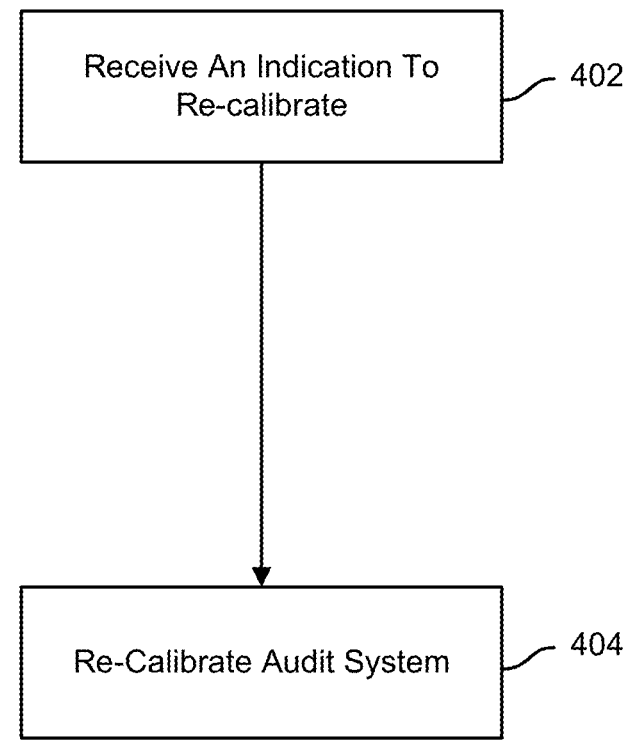
FIG. 4 is a flow diagram illustrating a process to recalibrate an audit system in accordance with some embodiments.

FIG. 4 is a flow diagram illustrating a process to recalibrate an audit system in accordance with some embodiments. In some embodiments, process 400 is implemented by a processor, such as processor 103.

At 402, an indication to recalibrate a sensor configuration is received. A device may include an accelerometer. An output associated with the accelerometer is monitored. An accelerometer output that differs from a baseline output by a threshold amount may indicate that a device that includes the accelerometer and one or more sensors has been moved or touched. The movement or touch may be deliberate or inadvertent. Regardless of the intent, the movement or touching of the device that includes one or more sensors may cause the one or more sensors to output non-calibrated values. As a result, the one or more machine learning models associated with a task may erroneously output a prediction having a confidence level above a threshold level because it was relying upon faulty sensor data.

In some embodiments, the indication is received from an evaluator of the audit system. The evaluator may perform an independent test of the audit system and determine that at least one machine learning model of the one or more machine learning models (or other mathematical model) associated with a task is erroneously outputting a prediction having a confidence level above/below the threshold level when the at least one machine learning model (or other mathematical model) should not be outputting a prediction having a confidence level above/below the threshold level. For example, the evaluator may swab a surface in a room and determine that it includes certain levels of a pathogen after the surface has been cleaned. The at least one machine learning model (or other mathematical model) may output a prediction having a confidence value indicating that the surface should not have the certain levels of the pathogen.

At 404, the audit system that includes a plurality of sensors and one or more machine learning models is recalibrated. In some embodiments, the one or more trained machine learning models are retrained. In some embodiments, some or all of the sensors associated with a task are modified or replaced. For example, a sensor may be out of position and no longer providing accurate measurements. A sensor may fail and need to be replaced. A sensor may provide inaccurate measurements because it needs new batteries. A component used in the process may have changed and the tasks associated may have also changed. Recalibrating the setup associated with the production environment ensures the one or more workers are accurately audited.

Figure 5:
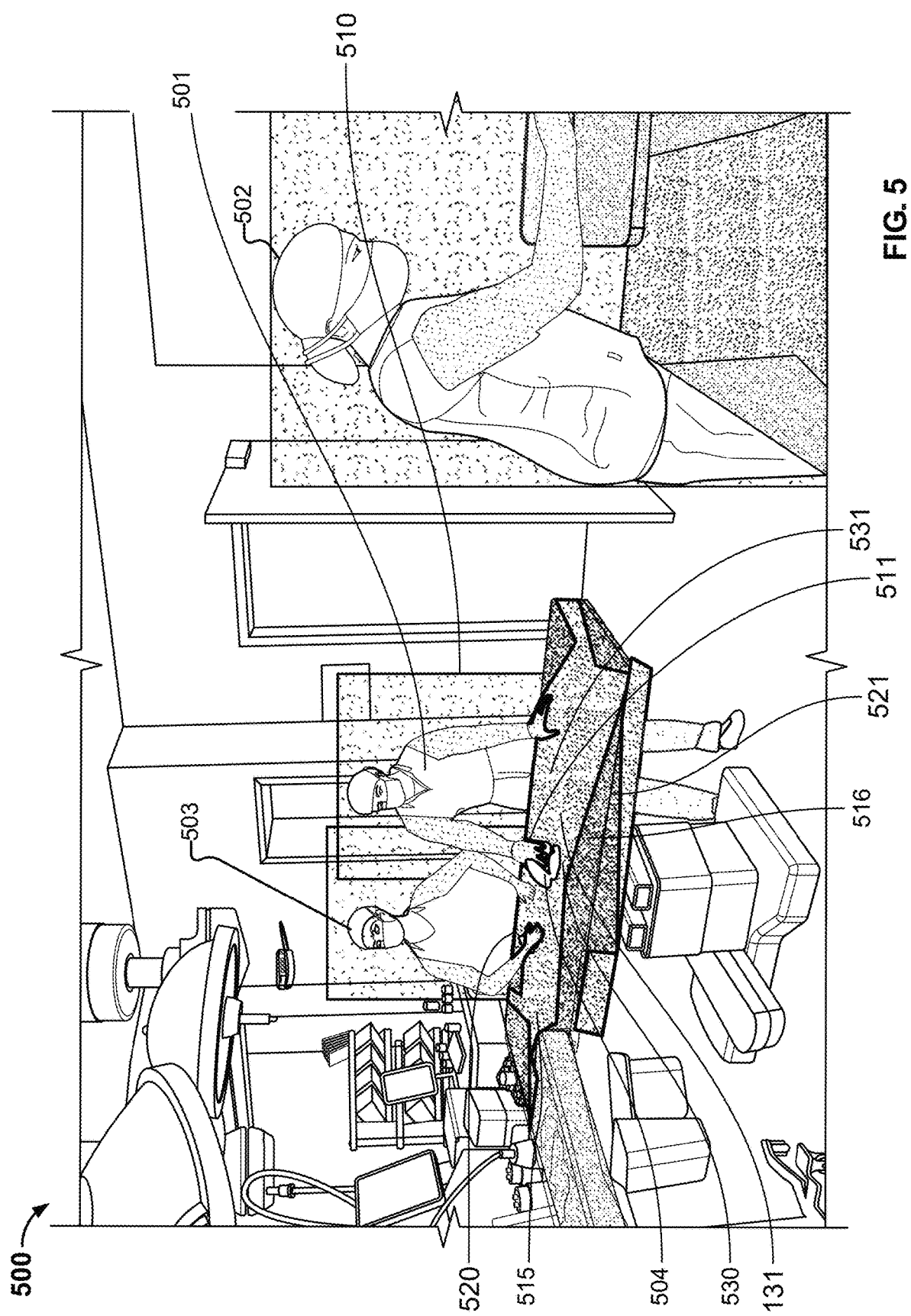
FIG. 5 depicts workers performing a task in a space in accordance with some embodiments.

FIG. 5 depicts workers performing a task in a space in accordance with some embodiments. In the example shown, workers 501, 502, 503 are performing a task of cleaning surfaces in space 500. In some embodiments, space 500 includes one or more devices (not shown), such as device 152a, 152b, that includes a plurality of sensors. In some embodiments, space 500 includes a first device, such as device 152a that includes one or more sensors and one or more other devices, such as device 152b, that includes one or more sensors. The device includes a processor that is configured to implement computer vision of workers 501, 502, 503 based on the sensor data while workers 501, 502, 503 are cleaning space 600. Although space 500 is depicted as a hospital room, space 500 may be an elevator, a waiting area, a hallway, a restaurant, a car, a train, a grocery store, a gym, a studio, a place of worship, a theater, a factory, . . . or other any human occupied space. The computer vision detects the three workers of the cleaning crew within space 500. For example, the processor implements computer vision to draw box 510 around worker 501. The processor implements computer vision to draw hand shape 511 around hand 504 of cleaner 501. The processor also implements computer vision to draw shape 520 around surface 515 which workers 501, 503 are currently cleaning.

The processor implements computer vision to track the movement of shape 511 (cleaner 501's hand) over shape 520 and records the locations within shape 520 that shape 511 has swiped with rag 530. The processor implements computer vision to perform the same tracking and recording for all three workers of the crew.

Once the workers 501, 502, 503 have finished cleaning and leave space 500, the processor may implement computer vision to identify the areas of shape 520 that no shapes 511 (e.g., hands) have wiped. Shape 521, drawn by computer vision, represents area 516 that the workers 501, 502, 503 missed. Workers 501, 502, 503 need to return to space 500 to clean the areas that it missed, such as shape 521 (i.e. area 516).

In some embodiments, computer vision is used to rate the quality of the overall cleaning effort. For example, a machine learning model that informs the computer vision may be trained using videos of thorough and effective cleaning in contrast to ineffective cleaning. This could be true not only for a task such as surface cleaning, but also for hand washing, floor cleaning, linen replacements, trash removal, and other such activities. In some embodiments, the computer vision in conjunction with data from a thermal sensor is utilized to determine whether the workers correctly performed the task of cleaning space 500.

The machine learning model might also be trained on a full complement of typical room cleaning processes, with the output of the model predicting the overall effectiveness of the effort. The trained machine learning model is configured to output a prediction having a confidence level above a threshold. For example, the output of the machine learning model could be the following: after the cleaning routine, the probability of surface pathogen levels above x amount is y percent. This estimate could also be tied to what the system has observed in the room previous to the cleaning. For example, factors that the model may consider include: an amount of time since a previous cleaning, a number of patients in the room since a previous cleaning, a duration in which a patient was in the room, a number of staff that has passed through the room since a previous cleaning, a duration in which each staff member was in the room, a number of cleaning measures that were applied, etc.

In some embodiments, the amount of activity in a particular area since the last cleaning is tracked. A particular area may include a bathroom, sink, or surface. Such data may be used to provide information to a cleaning crew before they begin, potentially increasing the effectiveness of their work.

In some embodiments, the cleaning crew uses a disinfecting solution that contains an invisible dye that can be picked up by a sensor. For example, the company GLO Effex sells a product it calls "Invisible Blue UV Reactive Water Dye." This water-soluble dye glows with a UV blacklight.

Figure 6:
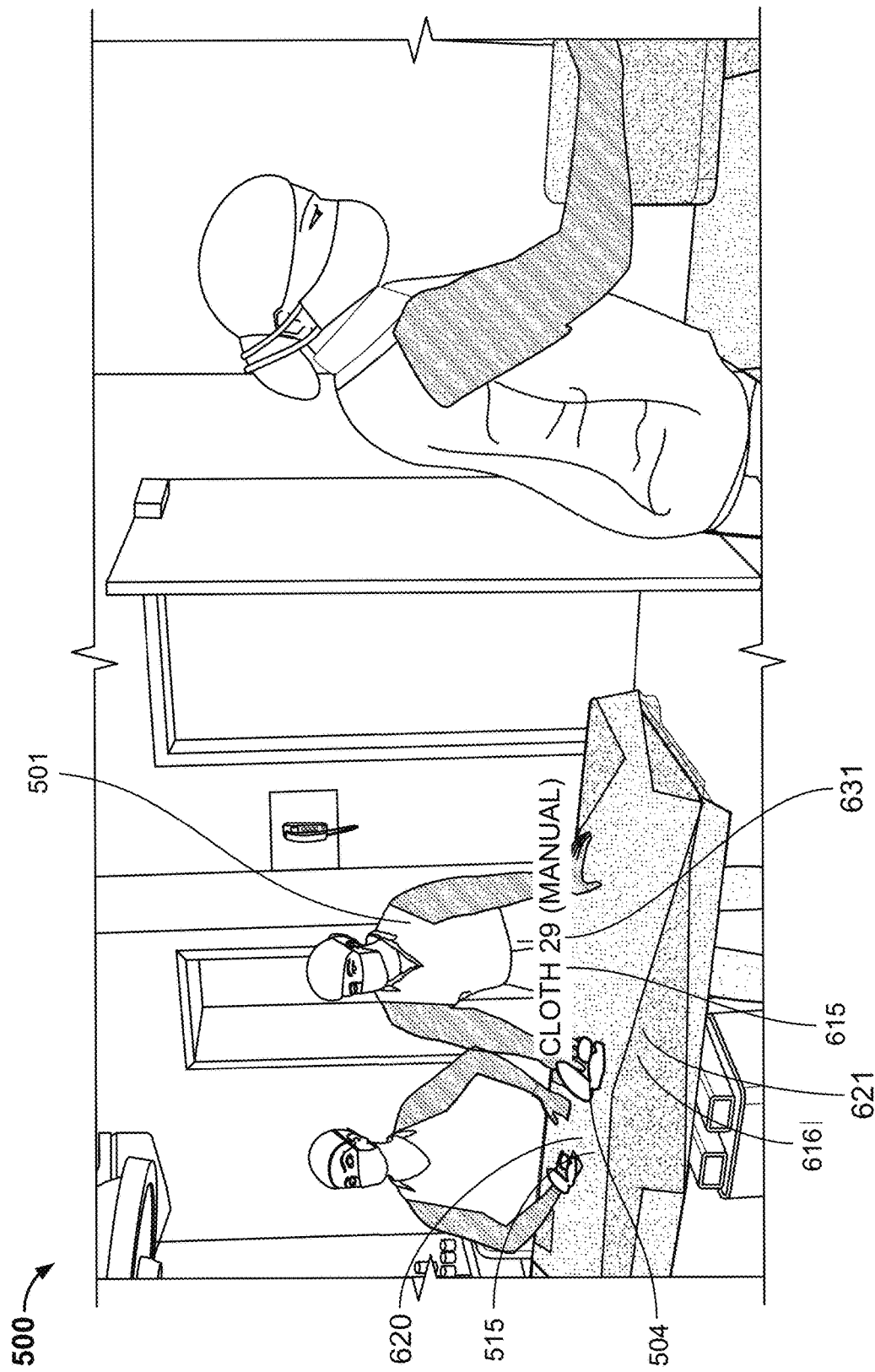
FIG. 6 shows workers performing a task in a space in accordance with some embodiments.

FIG. 6 shows workers performing a task in a space in accordance with some embodiments. In the example shown, worker 501 is in the midst of cleaning using a disinfecting solution that includes invisible dye. All three members of the crew are using this solution in their cleaning of space 500. For worker 501, sensor data shows the invisible dye 631 being present at area 615 that cleaner 501 has recently wiped. The sensor data also shows no invisible dye 621 present on area 616 that the crew missed.

Once the crew has finished cleaning space 500, the sensor data may be used to identify all the areas that the workers missed, namely, the areas revealing the absence of invisible dye. The workers need to return to space 500 to clean the areas that it missed, such as dye-less area 621.

Figure 7:
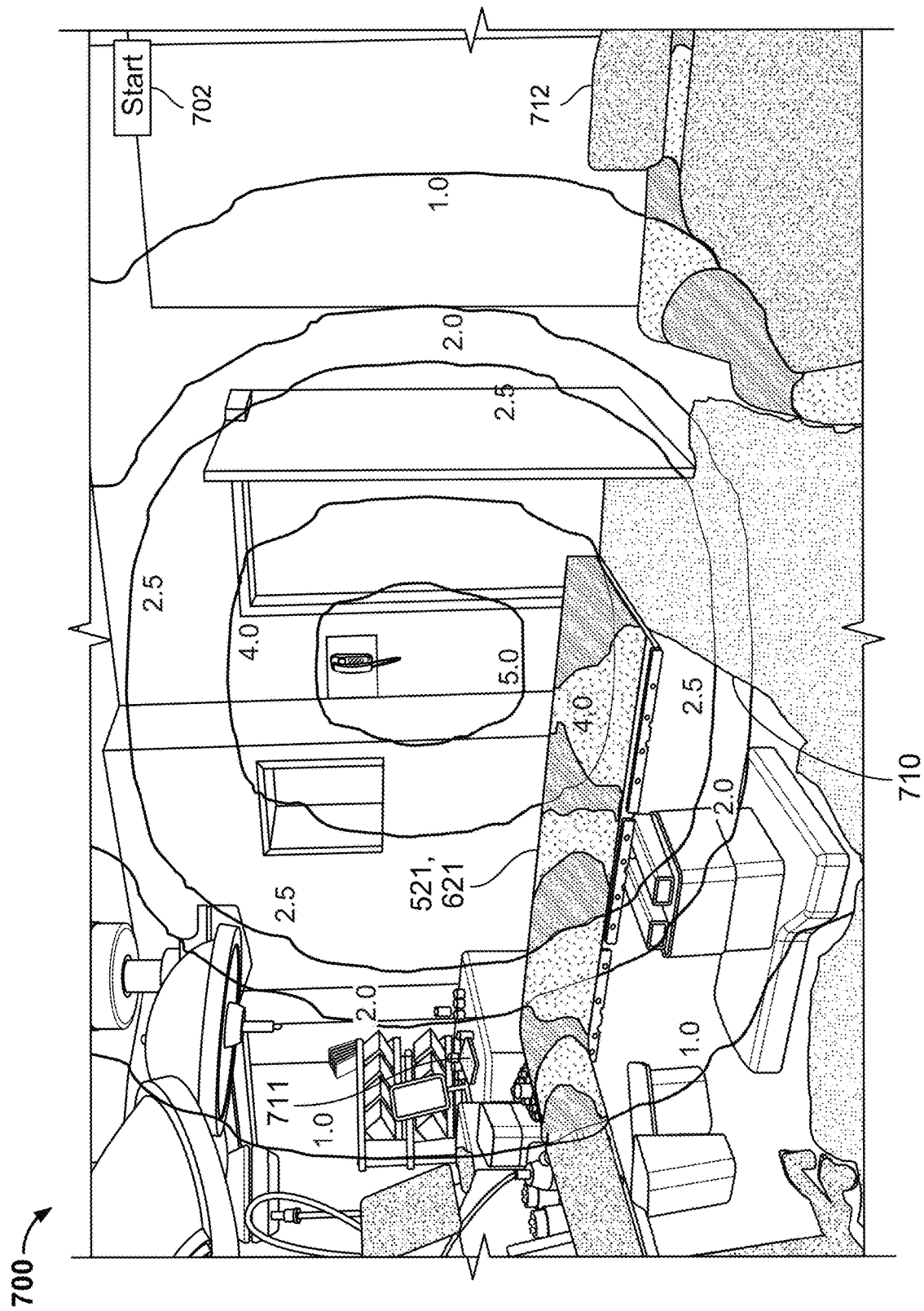
FIG. 7 depicts a notification in accordance with some embodiments.

FIG. 7 depicts a notification of a space in accordance with some embodiments. In the example shown, the notification may be provided to a device associated with a worker, such as device 106. The notification may be provided after a completion of a task. The notification provides an indication of the missed cleaning spots in space 500. In some embodiments, the missed spots are identified in various colors.

In some embodiments, the notification is provided as an image 700 on a device associated with one or more workers, such as a mobile phone, a smart device, a tablet, or on a page printed with the image(s). Using image 700, the worker(s) can quickly re-clean only the missed spots identified by the notification.

In some embodiments, multiple camera devices are deployed in a space, or a stereoscopic camera is used, providing different perspectives of the room. In these embodiments, a mobile app may create a 3D map of a space, which the one or more workers can manipulate to see from different angles and perspectives. The mobile app enables the ability to zoom in on a surface from different angles.

Image 700 includes missed spots 521, 621. These areas are patterned with a particular pattern since they are identified as the areas missed by the human cleaners on their most recent effort to clean the space.

Area 712 is shaded a particular shade (e.g., pink) to indicate that it is an area that might require additional disinfection by any form of disinfection (e.g., UV exposure, sending a person or robot to manually use chemical disinfectants, etc.).

Footpath 710 and surface 711 are shaded a particular shade (e.g., blue) to indicate they are high traffic areas; the former with footfalls, the latter with hand touches.

The notification may include a "start" button 702 that one or more workers of a cleaning crew press on the user interface of a device when they start the re-cleaning. This alerts the computer vision technology that the current cleaning effort is a re-cleaning rather than an original cleaning.

In some embodiments, the system automatically determines when the cleaners are engaged in a re-cleaning effort rather than an original cleaning. The system starts a countdown timer at the moment it sends the image to the mobile apps of the cleaners. The length of this timer can be defined as the time pathogens can reproduce or the time that a patient could effectively shed pathogens or re-contaminate a room through contact. Alternatively, the length of the timer can be set by an administrator of the space.

If one or more workers arrive at the space within the defined countdown time, the system assumes that the present cleaning effort is a re-cleaning process. Otherwise, the system assumes the cleaning effort is an original one with the entire room being the subject of the effort.

In some embodiments, once the cleaners complete the re-cleaning of the space, notification of this event is presented in their devices.

Figure 8:
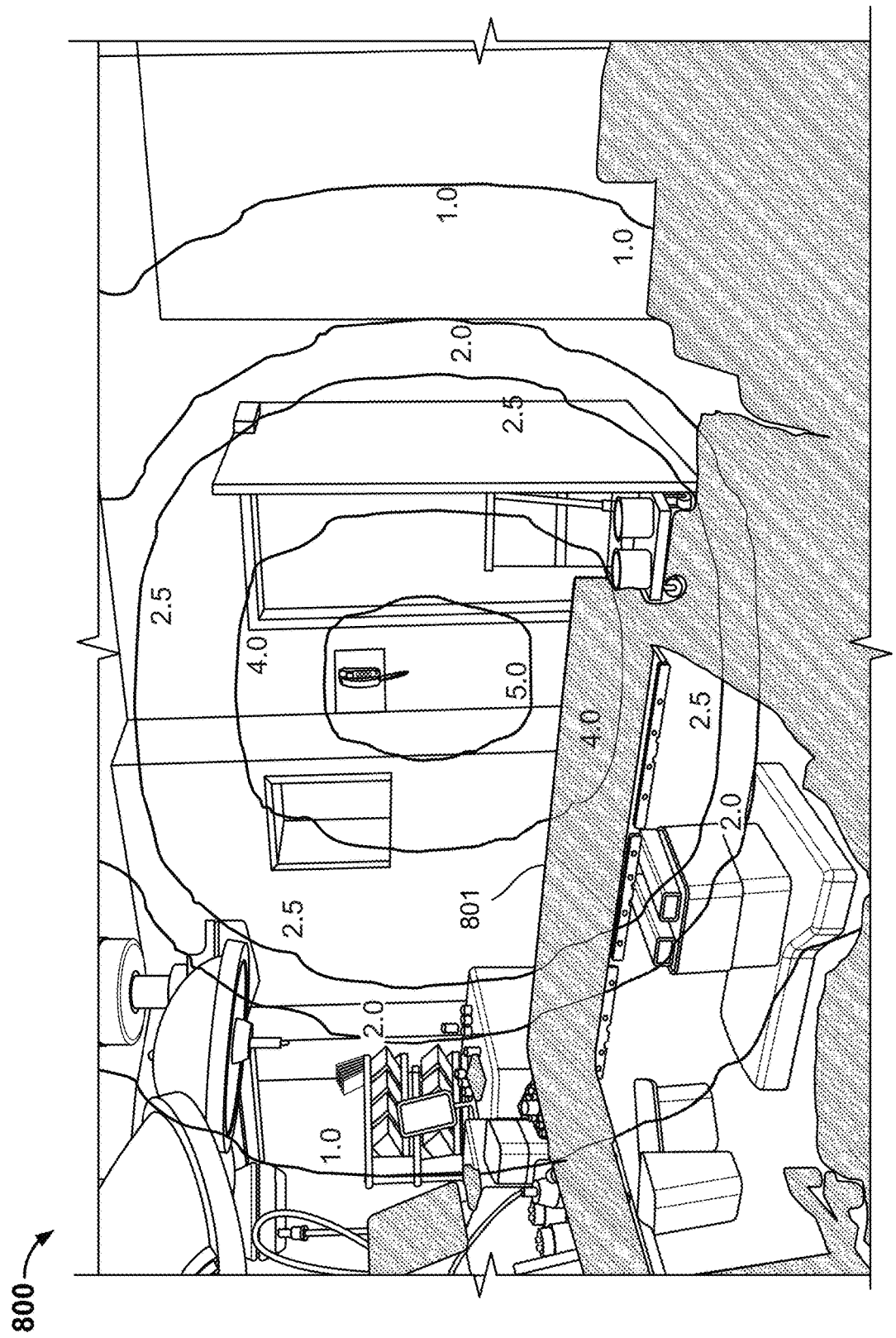
FIG. 8 depicts a notification in accordance with some embodiments.

FIG. 8 depicts a notification in accordance with some embodiments. For example, the mobile app can do one or more of playing a sound indicating completion, and replacing image 700 with image 800, showing fully re-cleaned the space, with re-cleaned surfaces 801 appearing in a shade indicating the surfaces are clean (e.g., green).

In some embodiments, assessments of the cleaners are provided to the cleaners and their managers. This assessment can include a ranking of the cleaners according to different criteria such as completeness, speed, and a combination of the two, with different factors possibly having different weights for the assessment.

In some embodiments, "gamification" is provided and presented to the cleaning staff and their managers. For example, bonuses/recognition are provided to crews and workers that clean in the allotted time and minimize the need for recleaning.

In some embodiments, feedback on the efficacy of the cleaning effort is provided in real-time, in an attempt to avoid the need for a subsequent cleaning effort. Such feedback includes one or more of audible beeps, spoken voice, illumination such as a spot light pointing at an area or surface. Such feedback is presented on one or more of the mobile app, and/or a TV in the room (which could display any number of views along with instructions).

Figure 9:
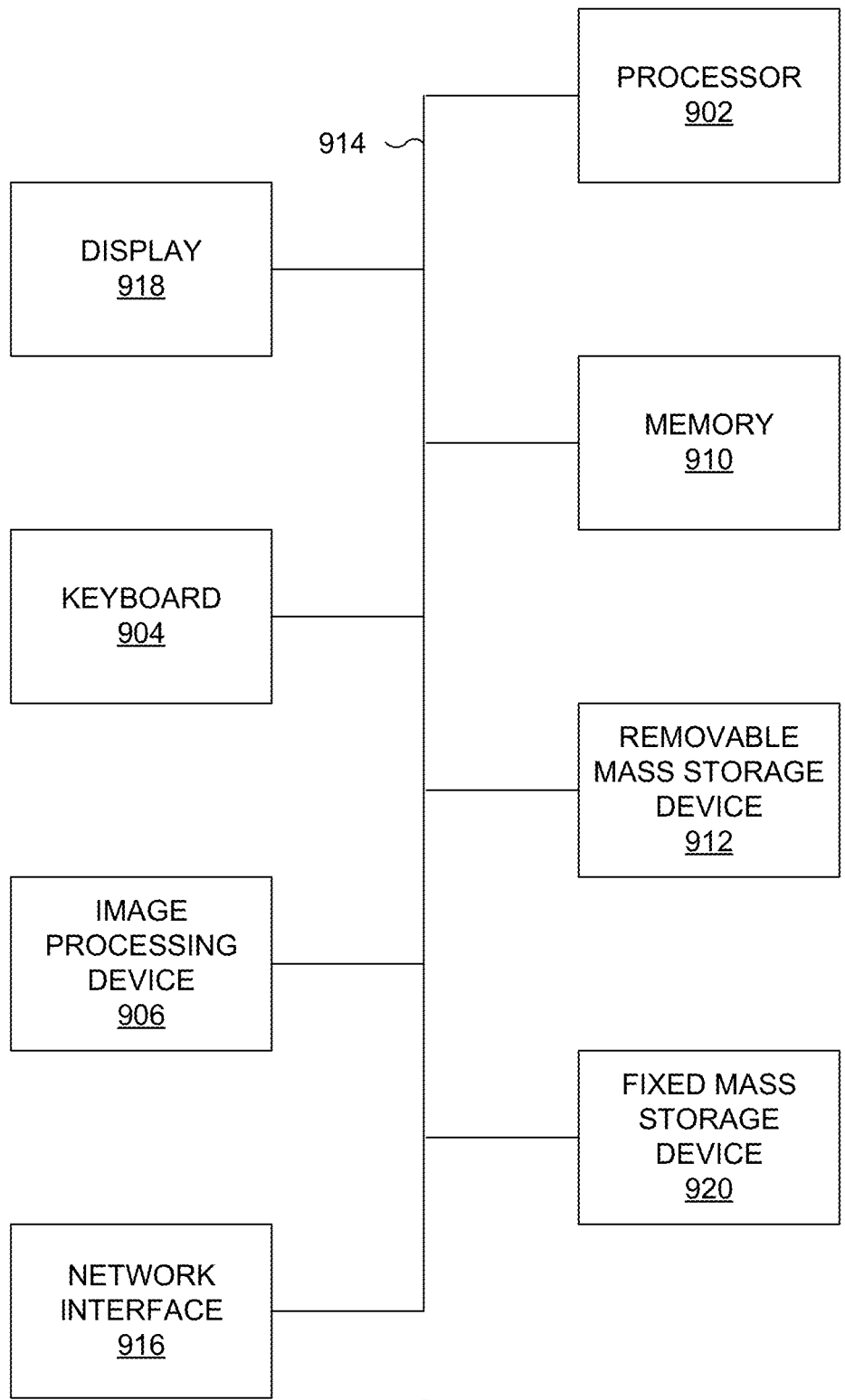
FIG. 9 is a functional diagram illustrating a server to audit a process performed by one or more workers in accordance with some embodiments.

FIG. 9 is a functional diagram illustrating a server to audit a process performed by one or more workers in accordance with some embodiments. As will be apparent, other server architectures and configurations can be used to perform the described product generation technique. Server 900, which includes various subsystems as described below, includes at least one microprocessor subsystem (also referred to as a processor or a central processing unit (CPU) 902). For example, processor 902 can be implemented by a single-chip processor or by multiple processors. In some embodiments, processor 902 is a general purpose digital processor that controls the operation of the server 900. In some embodiments, processor 902 also includes one or more coprocessors or special purpose processors (e.g., a graphics processor, a network processor, AI processor, etc.). Using instructions retrieved from memory 910, processor 902 controls the reception and manipulation of input data received on an input device (e.g., image processing device 906, I/O device interface 904), and the output and display of data on output devices (e.g., display 918).

Processor 902 is coupled bi-directionally with memory 910, which can include, for example, one or more random access memories (RAM) and/or one or more read-only memories (ROM). As is well known in the art, memory 910 can be used as a general storage area, a temporary (e.g., scratch pad) memory, and/or a cache memory. Memory 910 can also be used to store input data and processed data, as well as to store programming instructions and data, in the form of data objects and text objects, in addition to other data and instructions for processes operating on processor 902. Also as is well known in the art, memory 910 typically includes basic operating instructions, program code, data, and objects used by the processor 1702 to perform its functions (e.g., programmed instructions). For example, memory 910 can include any suitable computer readable storage media described below, depending on whether, for example, data access needs to be bi-directional or uni-directional. For example, processor 902 can also directly and very rapidly retrieve and store frequently needed data in a cache memory included in memory 910.

A removable mass storage device 912 provides additional data storage capacity for the server 900, and is optionally coupled either bi-directionally (read/write) or uni-directionally (read only) to processor 902. A fixed mass storage 920 can also, for example, provide additional data storage capacity. For example, storage devices 912 and/or 920 can include computer readable media such as magnetic tape, flash memory, PC-CARDS, portable mass storage devices such as hard drives (e.g., magnetic, optical, or solid state drives), holographic storage devices, and other storage devices. Mass storages 912 and/or 920 generally store additional programming instructions, data, and the like that typically are not in active use by the processor 902. It will be appreciated that the information retained within mass storages 912 and 920 can be incorporated, if needed, in standard fashion as part of memory 910 (e.g., RAM) as virtual memory.

In addition to providing processor 902 access to storage subsystems, bus 914 can be used to provide access to other subsystems and devices as well. As shown, these can include a display 918, a network interface 916, an input/output (I/O) device interface 904, an image processing device 906, as well as other subsystems and devices. For example, image processing device 906 can include a camera, a scanner, etc.; I/O device interface 904 can include a device interface for interacting with a touchscreen (e.g., a capacitive touch sensitive screen that supports gesture interpretation), a microphone, a sound card, a speaker, a keyboard, a pointing device (e.g., a mouse, a stylus, a human finger), a Global Positioning System (GPS) receiver, an accelerometer, and/or any other appropriate device interface for interacting with system 900. Multiple I/O device interfaces can be used in conjunction with server 900. The I/O device interface can include general and customized interfaces that allow the processor 902 to send and, more typically, receive data from other devices such as keyboards, pointing devices, microphones, touchscreens, transducer card readers, tape readers, voice or handwriting recognizers, biometrics readers, cameras, portable mass storage devices, and other computers.

The network interface 916 allows processor 902 to be coupled to, another computer, one or more robotic systems, computer network, a plurality of sensors, a network of storage bins, or telecommunications network using a network connection as shown. For example, through the network interface 916, the processor 902 can receive information (e.g., data objects or program instructions) from another network, or output information to another network in the course of performing method/process steps. Information, often represented as a sequence of instructions to be executed on a processor, can be received from and outputted to another network. An interface card or similar device and appropriate software implemented by (e.g., executed/performed on) processor 902 can be used to connect the server 900 to an external network and transfer data according to standard protocols. For example, various process embodiments disclosed herein can be executed on processor 902, or can be performed across a network such as the Internet, intranet networks, or local area networks, in conjunction with a remote processor that shares a portion of the processing. Additional mass storage devices (not shown) can also be connected to processor 902 through network interface 916.

In addition, various embodiments disclosed herein further relate to computer storage products with a computer readable medium that includes program code for performing various computer-implemented operations. The computer readable medium includes any data storage device that can store data which can thereafter be read by a server. Examples of computer readable media include, but are not limited to: magnetic media such as disks and magnetic tape; optical media such as CD-ROM disks; magneto-optical media such as optical disks; and specially configured hardware devices such as application-specific integrated circuits (ASICs), programmable logic devices (PLDs), and ROM and RAM devices. Examples of program code include both machine code as produced, for example, by a compiler, or files containing higher level code (e.g., script) that can be executed using an interpreter.

The server shown in FIG. 9 is but an example of a server suitable for use with the various embodiments disclosed herein. Other servers suitable for such use can include additional or fewer subsystems. In some servers, subsystems can share components (e.g., for touchscreen-based devices such as smart phones, tablets, etc., I/O device interface 904 and display 918 share the touch sensitive screen component, which both detects user inputs and displays outputs to the user). In addition, bus 914 is illustrative of any interconnection scheme serving to link the subsystems. Other computer architectures having different configurations of subsystems can also be utilized.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system, comprising:
a plurality of sensors configured to obtain data associated with one or more workers performing a task, wherein a first sensor of the plurality of sensors is an image sensor and a second sensor of the plurality of sensors is a thermal sensor; and
a processor coupled to the plurality of sensors and configured to:
process the data associated with the one or more workers, wherein computer vision is utilized to extract one or more features or patterns from image data obtained from the image sensor and to recognize gestures and/or actions performed by the one or more workers;
generate a feature vector that includes one or more sensor values associated with the second sensor and corresponding values associated with the one or more extracted features or the one or more extracted patterns;
input the feature vector to one or more models to determine whether the one or more workers correctly performed the task; and
output a notification indicating whether the one or more workers correctly performed the task based on an output of the one or more models.

2. The system of claim 1, wherein one or more other sensors of the plurality of sensors include a pressure sensor, a torque sensor, a temperature sensor, a radiation sensor, a proximity sensor, a position sensor, a flow sensor, a contact sensor, an acoustic sensor, a light sensor, a radar sensor, a millimeter wave sensor, an ultrasonic sensor, a touch sensor, an accelerometer, a humidity sensor, an infrared sensor, a color sensor, a gas sensor, a gyroscope, a hall sensor, a capacitive sensor, an analog sensor, a photoelectric sensor, a level sensor, a chemical sensor, an optical sensor, an active sensor, or a force sensor.

3. The system of claim 1, wherein the processor is configured to receive the data associated with the one or more workers performing the task.

4. The system of claim 3, wherein the processor is configured to pre-preprocess some or all of the data associated with the one or more workers performing the task.

5. The system of claim 4, wherein pre-processing some or all of the data associated with the one or more workers performing the task includes extracting one or more features or patterns.

6. The system of claim 5, wherein the one or more extracted features or patterns include edges, shapes, textures, colors, the gestures, and/or the actions.

7. The system of claim 5, wherein the one or more extracted features or patterns and the some or all of the data associated with the one or more workers is inputted to the one or more models trained to determine whether the one or more workers correctly performed the task.

8. The system of claim 1, wherein the notification is provided after the task is completed.

9. The system of claim 1, wherein the notification is provided to a device associated with the one or more workers.

10. The system of claim 1, wherein the notification includes one or more comments indicating why the one or more workers incorrectly performed the task.

11. The system of claim 1, wherein the notification includes one or more recommendations indicating what the one or more workers can do to correctly perform the task.

12. The system of claim 1, wherein the notification includes information indicating how to correctly perform the task.

13. The system of claim 1, wherein the notification is provided after completion of a process that includes the task.

14. The system of claim 1, wherein the processor is configured to receive an indication to recalibrate the one or more sensors and/or the one or more models.

15. The system of claim 14, wherein the processor is configured to recalibrate one or more of the one or more sensors and/or the one or more models in response to receiving the indication.

16. The system of claim 1, wherein the one or more models include one or more machine learning models trained using supervised learning, unsupervised learning, semi-supervised learning, or reinforcement learning.

17. The system of claim 1, further comprising an exciter to enhance the data associated with the one or more workers performing the task.

18. The system of claim 1, wherein one or more items are affixed to an object from which the one or more sensors are monitoring.

19. A method, comprising:
obtaining data associated with one or more workers performing a task, wherein the data associated with the one or more workers performing the task is obtained from a plurality of sensors, wherein a first sensor of the plurality of sensors is an image sensor and a second sensor of the plurality of sensors is a thermal sensor;

processing the data associated with the one or more workers, wherein computer vision is utilized to extract one or more features or patterns from image data obtained from the image sensor and to recognize gestures and/or actions performed by the one or more workers;

generating a feature vector that includes one or more sensor values associated with the second sensor and corresponding values associated with the one or more extracted features or the one or more extracted patterns;

inputting the feature vector to one or more models to determine whether the one or more workers correctly performed the task; and outputting a notification indicating whether the one or more workers correctly performed the task based on an output of the one or more models.

20. The method of claim 19, wherein one or more other sensors of the plurality of sensors include a pressure sensor, a torque sensor, a temperature sensor, a radiation sensor, a proximity sensor, a position sensor, a flow sensor, a contact sensor, an acoustic sensor, a light sensor, a radar sensor, a millimeter wave sensor, an ultrasonic sensor, a touch sensor, an accelerometer, a humidity sensor, an infrared sensor, a color sensor, a gas sensor, a gyroscope, a hall sensor, a capacitive sensor, an analog sensor, a photoelectric sensor, a level sensor, a chemical sensor, an optical sensor, an active sensor, or a force sensor.

21. A method, comprising:

obtaining data associated with one or more workers performing a task, wherein the data associated with the one or more workers performing the task is obtained from a plurality of sensors, wherein a first sensor of the plurality of sensors is an image sensor and a second sensor of the plurality of sensors is a thermal sensor;

processing the data associated with the one or more workers, wherein computer vision is utilized to extract one or more features or patterns from image data obtained from the image sensor and to recognize gestures and/or actions performed by the one or more workers;

generating a feature vector that includes one or more sensor values associated with the second sensor and corresponding values associated with the extracted features or the extracted patterns;

inputting the feature vector to one or more models to determine whether the one or more workers correctly performed the task; and outputting a notification indicating whether the one or more workers correctly performed the task based on an output of the one or more models.

22. A computer program product embodied in a non-transitory computer readable medium and comprising computer instructions for:

obtaining data associated with one or more workers performing a task, wherein the data associated with the one or more workers performing the task is obtained from a plurality of sensors, wherein a first sensor of the plurality of sensors is an image sensor and a second sensor of the plurality of sensors is a thermal sensor;

processing the data associated with the one or more workers, wherein computer vision is utilized to extract one or more features or patterns from image data obtained from the image sensor and to recognize gestures and/or actions performed by the one or more workers;

generating a feature vector that includes one or more sensor values associated with the second sensor and corresponding values associated with the one or more extracted features or the one or more extracted patterns;

inputting the feature vector to one or more models to determine whether the one or more workers correctly performed the task; and outputting a notification indicating whether the one or more workers correctly performed the task based on an output of the one or more models.

* * * * *